United States Patent [19]

Adams et al.

[11] Patent Number: 5,190,860
[45] Date of Patent: Mar. 2, 1993

[54] DIFFERENTIAL DIAGNOSTIC ASSAY FOR BRUCELLOSIS

[75] Inventors: Leslie G. Adams; Roger Smith III; Joe W. Templeton, all of College Station, Tex.; Kathleen A. Overholt, Silver Spring, Md.

[73] Assignee: The Texas A & M University System, College Station, Tex.

[21] Appl. No.: 428,825

[22] Filed: Oct. 30, 1989

[51] Int. Cl.$^5$ ................ G01N 33/569; G01N 33/577; C07K 15/28; C12N 5/00
[52] U.S. Cl. .................................... 435/7.32; 435/7.5; 435/7.9; 435/7.93; 435/240.27; 435/975; 436/518; 530/388.4; 530/810; 530/825
[58] Field of Search ..................... 435/7.5, 7.32, 7.9, 435/7.92, 7.93, 172.2, 240.26, 975; 436/548; 424/88; 530/387, 388.4, 810, 825

[56] References Cited

U.S. PATENT DOCUMENTS 4,228,237 10/1980 Hevey et al. .................. 435/7.94
5,006,463 4/1991 Cherwonogrodzky et al. ... 435/7.32

OTHER PUBLICATIONS

P. Tijssen, Practice and Theory of Enzyme Immunoassays, pp. 21–31 (1985).

Primary Examiner—Mary E. Ceperley
Assistant Examiner—Carol E. Bidwell

[57] ABSTRACT

An immunoassay procedure is provided which exhibits increased specificity over current procedures. The procedure allows the differentiation of animals infected with *Brucella abortus* from animals vaccinated with *Brucella abortus* Strain 19. The invention employs unique monospecific monoclonal antibodies having particular affinity, specificity and binding characteristics directed to a *B. abortus* lipopolysaccharide antigen. The invention also concerns continuous hybrid cell lines for producing the unique monoclonal antibodies.

10 Claims, No Drawings

DIFFERENTIAL DIAGNOSTIC ASSAY FOR BRUCELLOSIS

FIELD OF THE INVENTION

The present invention pertains to immunological procedures and corresponding reagents for the diagnosis of brucellosis in animals. More specifically, the invention relates to the discovery of unique monospecific antibodies to an antigenic determinant of a *Brucella abortus* lipopolysaccharide molecule and continuous cell lines capable of producing and secreting the monoclonal antibodies. In addition, the invention comprises methods for the differential diagnosis of animals infected with field strains or Strain 19 of *Brucella abortus* and animals vaccinated with *B. abortus* Strain 19.

BACKGROUND OF THE INVENTION

*Brucella abortus* (hereinafter "*B. abortus*") is a bacterial organism which causes brucellosis which is characterized by spontaneous abortion and chronic infection within the lymph nodes and in the mammary glands of animals such as cattle or bison. This disease causes extensive economic loss due to abortion, the birth of weak debilitated calves, decreased milk production and infertility.

To reduce the incidence and economic loss caused by brucellosis, animals are often vaccinated with either live or killed organisms of *B. abortus.* Production of antibodies specific for *B. abortus* is a serological defense against bovine brucellosis and is the partial premise for prophylactic vaccination. The vaccine of choice is the attenuated *B. abortus* strain 19, which like the field Strain 2308, is strongly antigenic. Unfortunately, a consistently effective means for distinguishing Strain 19 vaccinated animals from those infected by pathogenic strains of *B. abortus* or Strain 19 is not available. Both the vaccine and the pathogenic strains stimulate the production of cross-reacting antibodies which serve as the basis for current serological tests for brucellosis. Hence, the current serological tests are often unable to distinguish Strain 19 vaccinated animals from field strain or Strain 19 infected animals, including cattle and bison. Inaccurate diagnosis often results in economic losses due to unnecessary testing of herds and unnecessary quarantine of cattle which in turn inhibits the movement and marketing of cattle through livestock marketing systems. Thus, a need exists for an assay which is capable of distinguishing between infected and vaccinated animals.

The current procedures used to detect antibodies stimulated by *B. abortus* include the card test, rivanol, particle concentration fluorescence immunoassay (PCFIA), hemolysis-in-gel (HIG), complement fixation (CF) and the indirect enzyme-linked immunosorbant assay (ELSIA). However, none of these current tests have proven to be effective in differentially detecting Strain 19 stimulated antibodies versus field strain stimulated antibodies.

The antibodies detected by the CF and ELISA tests correlate closely with the presence of disease. Unfortunately, even these tests can not detect all infected cattle without giving false positive reactions in uninfected cattle. Hence, in practice, the serological testing component of a brucellosis eradication program often consists of a combination of serological tests. The inefficiency and often contradictory results of these combined procedures often affect the progress toward eradication of the disease.

For diagnostic usefulness, a definitive test must have a high degree of accuracy in successfully identifying both:

(1) infected animals in a diseased population (high sensitivity); and (2) disease-free individuals in a healthy population (high specificity).

The sensitivities reported for the current CF and ELISA procedures range from 86–93% and 87–89% respectively. Similarly, the specificities reported for these two tests respectively are 93–99% and 26–51%.

Recently, two ELISA procedures have been proposed to differentiate between vaccinated and infected cattle. More specifically, a first ELISA assay system for differentially detecting antibodies stimulated by Strain 19 vs. field strains utilized a monoclonal antibody to *Yersinia enterocolitica* 0:9 smooth lipopolysaccharide antigen. However, this assay lacked sufficient sensitivity because it failed to detect cattle infected with low doses of field Strain 2308 of *B. abortus* (see Nielsen et al., Am. J. Vet. Res., Vol 50, No. 1, (1989) 5–9). A second ELISA procedure utilized a monoclonal antibody to *B. abortus* 544 smooth lipopolysaccharide antigen. However, this assay lacked sufficient specificity as it failed to differentiate at least 10% of vaccinated cattle from infected cattle. Also, the assay is based upon a cumbersome ELISA procedure which offers a limited possibility for mass-scale production (see Chin et al., Vet. Immunol. Immunopathol., Vol. 20, (1989) 109–118).

SUMMARY OF THE INVENTION

The present invention is directed to the provision of novel monospecific monoclonal antibodies (Mabs) and their use in immunoassay procedures to detect and differentiate antibodies stimulated by *B. abortus* infection from antibodies stimulated by *B. abortus* Strain 19 vaccination, thus permitting accurate field strain diagnosis and eliminating false positive results caused by Strain 19 vaccination. Thus, the present invention also relates to the discovery that utilizing Mabs having particular binding and affinity characteristics and which are directed to a particular epitope of a *B. abortus* lipopolysaccharide (LPS) antigen facilitate the differential diagnosis of brucellosis.

The present invention comprises novel Mabs and hybrid cell lines produced by hybridoma cell-fusion technology which are characterized by: (1) extremely high affinity Mabs, (2) with specificity for the immunodominant *B. abortus* lipopolysaccharide "O"- side chain (n-formyl-perosamine), (3) very stable hybridoma cell lines, (4) Mabs with high structural stability to withstand chemical conjugation procedures, and which are (5) uniquely able to competitively inhibit the binding of polyclonal antibodies normally induced by Strain 19 vaccination while not effectively competing with polyclonal antibodies stimulated by field strain or persistent Strain 19 infection.

The present invention also concerns immunoassay procedures which are both highly specific and highly selective in detecting and differentiating between animals, such as cattle or bison, infected with *B. abortus* and healthy animals. The immunoassays of the present invention have similar or superior sensitivity and greatly increased specificity over prior techniques. It is envisioned that the present invention may utilize a variety of assay procedures including ELISA in both homogenous and heterogenous environments. The assay procedures may be conducted on samples such as blood serum, milk, or any other body fluid containing antibodies.

In one aspect, an amplified competitive ELISA (cELISA) procedure utilizing the monospecific Mabs. according to the present invention is employed. The Mabs uniquely compete with antibodies induced by vaccination of Strain 19, but not antibodies induced in cattle and bison by infection with *B. abortus* field strains or Strain 19. This allows not only serologic diagnosis of brucellosis, but differentiation of vaccination from infection in a single assay for the first time. The Mab cELISA procedure may be performed on standard blood serum samples or any body fluids or secretions containing antibodies. The Mab cELISA procedure may employ any number of commercially available fixed or portable-manual, semi-automated or robotics-automated ELISA equipment with or without computer assisted data analysis reduction software and hardware.

Other objects and advantages of the invention will become readily apparent from the ensuing description

DETAILED DESCRIPTION OF THE INVENTION

Mice were immunized with *B. abortus* Strain 2308 to stimulate the lymphocyte population to produce antibodies to antigens associated with the field strain pathogen. Fusion of mouse splenocytes from the in vivo immunized mice with the myeloma cell line SP 2/0 produced hybrid continuous cells ("hybridomas"). The hybridomas which produced and secreted antibodies directed to epitopes of the "O" side chain of *B. abortus* antigens were selected utilizing ELISA, indirect fluorescent antibody, $^{125}$iodinated protein A, and Western blot assays.

Over 200 hybridoma cell lines were selected by the above procedures. Quite surprisingly, the hybridoma cell line identified as No. 39 produced and secreted a monoclonal antibody (Mab No. 39) having a higher affinity ($7.8\times10^{10}$ liters per mole) and which competed more effectively for the "O" antigen side chain on the lipopolysaccharide of *B. abortus* than any of the other antibodies which were screened Moreover, monoclonal antibody No. 39 more effectively competed against USDA *B. abortus* Strain 19 vaccine induced bovine polyclonal antibodies while competition against *B. abortus* field strain stimulated bovine polyclonal antibodies was not evident.

Based upon this discovery, Mab No. 39 can be used to identify other antibodies having the same or similar characteristics by following the cloning and competition procedures mentioned above. Therefore, although the present invention is often described in relation to hybridoma cell line No. 39 and Mab No. 39, it will be understood that the present invention is directed to the discovery that monoclonal antibodies having particular specificity, affinity and binding characteristics, i.e. those similar to Mab No. 39, may be employed in differential diagnostic procedures to accurately distinguish between healthy (or vaccinated) and diseased animals. Hence, useful antibodies according to the invention are not limited to a particular isotype, although IgG immunoglobins are usually preferred.

Based upon the above description, a fully functional competitive ELISA assay has been developed and is operational on an automated robotics workstation (Beckman Biomek) as well as on Dynatek ELISA equipment. This assay has been tested on over 600 bovine sera of confirmed known status and demonstrated to have an overall specificity of 99.6% and a sensitivity of 92.9% for detecting and differentiating field strain vs. vaccine induced antibody activity in cattle. The assay may also be adapted for use as a field (chute-side) competitive ELISA assay using hand-held battery-operated ELISA strip reading spectrophotometer. Mab No. 39 has been fully developed in a complete differentially diagnostic competitive ELISA assay ready for production and commercialization on a large scale. Mab No. 39 has already been immunologically characterized, adapted to tissue culture and ascites production, conjugated, titrated, optimized, stored as frozen stable cell lines, implemented with precision in an optimized competition-based ELISA method and fully evaluated and validated with serums from cattle of confirmed disease or vaccination status. Monoclonal antibody No. 39 has been produced in larger quantities using defined medium in laboratory-scale experiments and the monoclonal antibody production by hybridoma cell line No. 39 was shown to be stable by the procedures previously mentioned after greater than five recloning cycles. Furthermore, monoclonal antibody No. 39 is stable when subjected to biochemical manipulations. Thus, it is envisioned that the antibodies employed in the methods of the present invention may be labeled using any standard technique such as fluorescent tagging, biotinylation, radio-labeling, direct enzyme conjugation (e.g. horse radish peroxidase, alkaline phosphatase, bacterial luciferase, etc.), or other comparable conjugation procedures.

EXAMPLES

The following examples are presented to describe preferred embodiments and utilities of the present invention but should not be construed as limiting the claims thereof.

EXAMPLE 1

This example illustrates the methods for the preparation and selection of the hybridoma cell line No. 39 and corresponding monoclonal antibody.

A. Media

Maintenance medium contained Dulbecco's modified Eagle's medium (DMEM) with high glucose (4.5 g/liter) (KC Biological Inc., Lenexa, Kans.) supplemented with sodium bicarbonate (3.7 g/liter), 15% heat inactivated fetal bovine serum (FBS) (Sterile Systems Inc., Logan Utah) and 50 μM 2-mercaptoethanol (Sigma Chemical Co., St. Louis, Mo.). Fusion medium contained equal parts (v/v) of polyethylene glycol (PEG) 1000 (Sigma Chemical Co., St. Louis, Mo.) and DMEM. Hybridoma medium contained DMEM with high glucose supplemented with 4 mM L-glutamine, 1 mM sodium pyruvate, 100 uM minimum essential medium non-essential amino acids 100 U/ml penicillin and 100 ug/ml streptomycin (Gibco, Grand Island, N.Y.), 50 μM 2-mercaptoethanol, 18 mM Hepes buffer (Sigma Chemical Co., St. Louis, Mo.), 18% heat inactivated FBS and 2% Type 100 rabbit serum (Quadroma, Inc., Escondido, Calif.) HAT medium contained hybridoma medium with hypoxanthine ($1\times10^{-4}$ M), aminopterin ($4\times10^{-7}$ M) and thymidine ($1.6\times10^{-5}$ M) HT medium was HAT medium which did not contain aminopterin.

B. Feeder Layers

Peritoneal exudate cells (PEC) were collected in 11.6% sucrose by peritoneal lavage from BALB/C mice and washed three times by centrifugation ($100 \times g$ for 8 min.) in serum-free DMEM. After the final centrifugation, the supernatant fluid was removed, and the cells were resuspended in HAT medium at a concentration of $4 \times 10^5$ PEC/ml. Each well of ten 96-well microtiter plates (Flow Laboratories, McLean, Va.) received 50 µl and the plates were incubated at 37° C. in an atmosphere of 7.6% $CO_2$ for 12-24 hours prior to use.

C. Preparation of Myeloma Cells for Fusion

The murine non-immunoglobulin secretor myeloma cell line Sp2/0-Ag14 was obtained from the Salk Institute (Cell Distribution Center, San Diego, Calif.) and was demonstrated to be free of Mycoplasma by Hoechst 33258 fluorescent staining (Chen, 1977) and ultrastructural examination. The cell line was cultured routinely in maintenance medium at 37° C. in an atmosphere of 7.5% $CO_2$. Prior to fusion with spleen cells, it was subcultured at least 3 times in maintenance medium containing 15 µg/ml 8-azaquanine (Sigma Chemical Co., St. Louis, Mo.). Myeloma cells in exponential growth phase were transferred to 50 ml conical centrifuge tubes, and washed twice with serum-free DMEM. The viability of the myeloma cells was checked with ethidium bromide-acridine orange stain. Dilutions were made so that $10^7$ viable myeloma cells were contained in 10 mls of serum-free DMEM.

D. Immunization of Mice

*Brucella abortus* Strain 2308 (Generously provided by Dr. B. L. Deyoe, United States Department of Agriculture, Science and Education Agency, National Animal Disease Center, Ames, Iowa) was grown in tryptose broth (Difco Laboratories, Detroit, Mich.) at 37° C. for 2 days with 5% $CO_2$, following which 10 ml of this broth was subcultured in liter flasks (150 cm² surface area) containing 50 ml/flask of trypticase soy agar (Baltimore Biologicals Laboratories, Baltimore, Md.). After 2 days incubation, the bacteria were harvested with 10 ml sterile distilled water, washed three times by centrifugation ($7800 \times g$ for 15 min. at 40° C.) and resuspended in sterile phosphate buffered saline (PBS) at the appropriate concentration. Sendai virus free six-week-old female BALB/c mice (Jackson Laboratories, Bar Harbor, Me.) were injected intraperitoneally with 1.0 ml of PBS containing $1 \times 10^9$ colony forming units of whole *B. abortus* Strain 2308 bacteria irradiated with 1.38 megarads of $^{60}$Co. (Contributed by Dr. R. D. Neff, Department of Biochemistry, Biophysics and Nuclear Science, Texas A & M University, College Station, Tex.). Twenty-one days later, mice having anti-Brucella precipitin titers greater than or equal to 1:5000 were injected intravenously with 0.1 ml of PBS containing the same quantity and type of bacteria as were injected previously.

E. Preparation of Spleen Cells for Fusion

Four days following the intravenous injection, two mice were killed by cervical dislocation, immersed in 70% ethanol, and their spleens were removed and washed five times in petri dishes containing 5 ml each of serum-free DMEM. They were then pressed through a stainless steel screen using the rubber plunger of a sterile disposable 12 ml plastic syringe into a petri dish containing 3 ml of serum-free DMEM . The "spleen socks" were left on the screen. The suspension was pipetted up and down several times with a 5 ml pipette to break up clumps of cells. The cell suspension was placed in a 50 ml conical centrifuge tube and centrifuged at $400 \times G$. for 10 min. The spleen cells were washed twice with serum-free DMEM. The viability of the cells was checked with ethidium bromide-acridine orange stain. The cells were diluted so that $10^8$ viable spleen cells were contained in 10 mls of serum-free DMEM.

F. Production of Hybrid Cells (Fusion Technique)

The suspensions of $10^7$ viable myeloma and $10^8$ viable spleen cells were combined and centrifuged for 10 min. at $400 \times g$ to obtain a mixed pellet. The supernatant fluid was removed and the tube was tapped gently to loosen the pellet into a clumpy slurry of cells. The cells were then fused by slowly adding 0.8 ml of 50% polyethylene glycol (molecular weight 1000) in serum-free DMEM over a period of one min. The mixture was left undisturbed for one min. followed by stepwise dilution in 21 mls of serum-free DMEM over a period of about five min. The cells were centrifuged and resuspended in 35 mls of complete DMEM +HAT in a 75 cm² flask (Costar, Cambridge, Mass.). On the following day an additional 15 mls of the same medium were added to the flask, and the cells were distributed in 0.05 ml aliquots over feeder layers of mouse peritoneal exudate cells in 10 96-well plates. On the seventh day after the fusion 0.1 ml of complete DMEM+HT was added to every well, and on the tenth day 0.1 ml of supernatant fluid was removed from every well and replaced with 0.1 ml of complete DMEM+HT. Between days 10 and 24 after fusion, supernatant fluids from wells containing hybridomas with approximately 50% confluent growth were tested for anti-brucella activity. For a general discussion of cell fusion procedures see Galfre, et al., Nature, Vol. 266, (1977) 550-552.

G. Analysis of Hybridomas

Supernatant fluids were assayed for anti-brucella antibody activity by solid phase enzyme-linked immunosorbent assay (ELISA) (Byrd et al. 1979), using peroxidase-labeled affinity purified goat-antimouse IgG and IgM (Kirkgaard & Perry Laboratories, Gaithersburg, Md.), and the optical density at 405 nm was determined in a MR580 Microensa Auto Reader or a 290 Manual Reader (Dynatech Laboratories, Alexandria, Va.). The antigenic preparation for detecting antibodies consisted of a suspension of $10^9$ irradiated (1.38 megarads-$^{60}$Co) whole cells from *B. abortus* Strain 2308 per Well in ammonium acetate-ammonium carbonate buffer (pH 8.2) dried in 12 well detachable polystyrene (Immulon 11 Removawell) strips (Dynatech Laboratories, Alexandria, Va.).

H. Cloning of Hybridomas

In an effort to assure that the antibody secreted by a hybridoma is in fact monospecific, it is necessary to disperse the population of cells so that a cell line can be established from a single cell. Hybridomas that were producing antibodies to *B. abortus* Strain 2308 were selected and recloned by a modification of the limiting dilution method of Oi and Hertzenberg (Oi, V. T. and Hertzenberg, L. A., 1980, "*Immunoglobin-Producing Hybrid Cell Lines*", In: B. B. Mishell and S. S. Shiigi ed., *Selected Methods in Cellular Immunology*, W. H. Freeman and Co., San Francisco, pp. 351-372).

I. Selection of Hybridoma (and Mab) No. 39

Four or more subcloning procedures of the hybridoma cell lines were repeated un&il the clones consistently produced large quantities of monoclonal antibodies as detected by the above mentioned solid phase ELISA procedure. The monoclonal antibodies produced from the cloned hybridoma cell lines were then evaluated as native unconjugated versus biotin conjugated antibodies and vice versa in a classical competitive checkerboard-type assay. Antibodies were competed against each other to select the antibody with the highest relative percentage of inhibition of binding to *B. abortus* lipopolysaccharide. The results of the competition were determined by avidin-horse radish peroxidase bound activity with a standard substrate at an optical density of 405nm. After monoclonal antibodies were selected by the checkerboard competitive assay, affinity constants were estimated using the standard Scatchard plot analysis with data derived from the optical density values of a solid phase ELISA procedure (Scatchard, G., "*The attractions of Proteins for Small Molecules and Ions.*", Am. N.Y., Acad. Sci., Vol. 51 (1949) 660-672).

Out of the over 200 hybridoma cell lines that were selected in step H. above, the hybridoma cell line identified as No. 39 produced and secreted an antibody (Mab No. 39) which competed most effectively for the *B. abortus* LPS antigen. Hybridoma cell line No. 39 was deposited with the American Type Culture Collection on Oct. 26, 1989, and was assigned deposit No. HB10286.

Following the above mentioned Scatchard analysis, the affinity constant for Mab No. 39 was determined to be $7.8\times10^{10}$ liters per mole. The isotype of Mab No. 39 was determined to be $IgG_1K$ using an ELISA procedure (Zymed murine immunoglobin isotyping Kit, Zymed Co., South San Francisco, Calif.).

EXAMPLE 2

This example is directed to the isolation and selection of additional antibodies having properties similar to Mab No. 39.

Steps of A-H of Example 1 may be repeated as set forth above. After clones producing monoclonal antibodies to *B. abortus* 2308 are selected, they may be subjected to a solid phase ELISA classical competitive checkerboard-type assay using Mab No. 39 as a reference. A possible assay may appear as follows:

| | | Mab No. | | | |
|---|---|---|---|---|---|
| | | 39* | A* | B* | C* |
| Mab NO. | 39** | 100# | 97 | 96.0 | 97.0 |
| | A** | 100 | 97 | 85.0 | 0.0 |
| | B** | 96 | 72 | 92.0 | 43.0 |
| | C** | 2.6 | 0.0 | 0.0 | 64.0 |

*Unconjugated
**Biotinylated
Percent competition normalized to No. 39 competing with No. 39

From the above table, antibodies A and B would be selected for further screening, while antibody C would not. The antibodies selected following the above procedure, would then be screened for isotype, stability of the Mab during chemical conjugation, stability of the hybridoma for long term production, specificity, and affinity constant following the procedures of Example 1. A monoclonal antibody could be produced having similar specificity and binding characteristics to Mab No. 39 following the protocol outlined above.

EXAMPLE 3

This example is directed to a competitive ELISA procedure utilizing Mab No. 39 isolated from hybridoma cell line No. 39 prepared above.

A. Biotinylation Procedure

1. Chemicals a. Biotin—for biotinylation is N-hydroxysuccinimido-biotin (NHS-biotin) from Sigma.

b. Dimethyl Sulfoxide (DMSO)—High Pressure Liquid Chromatography (HPLC)-grade DMSO from Aldrich.

c. Sodium bicarbonate—anhydrous $NaHCO_3$ from Sigma.

d. Monobasic potassium phosphate—$KH_2PO_4$ from Sigma.

e. Dibasic sodium phosphate—$Na_2HPO_4$ from Sigma.

f. Sodium chloride—NaCl from Sigma.

g. Dialysis Tubing—seamless regenerated cellulose—average pore permeability of 24 angstroms—Van Waters and Rogers Scientific Co.

2. Working Solutions a. Monoclonal antibody—concentration of monoclonal antibody from the culture supernatant in serum-free media should be concentrated by ultrafiltration to 1 mg per ml. The monoclonal antibody concentration is estimated using the Bradford kit from Biorad.

b. The NHS - biotin DMSO solution is made by dissolving 1 mg of NHS-biotin per ml of DMSO.

c. The 0.1M sodium bicarbonate is made by dissolving 0.84 mg of $NaHCO_3$ per ml of distilled water. Adjust pH to 8.2 using $NaHCO_3$ to raise the pH and 0.1N Hydrochloric acid to lower the pH.

d. Phosphate buffered saline (PBS) pH7.2. Solution A. 9.08 gms $Kh_2PO_4$+9.0 gms of NaCl dissolved in enough distilled water to make up 1,000 mls total volume Solution B. 9.47 gms $Na_2HOP_4$+9.0 gms of NaCl dissolved in enough distilled water to make up 1,000 mls total volume. To make 1,000 mls of PBS, add 300 mls of Solution A to 700 mls of Solution B. CheckpH of the mixture of Solution A and B. The working pH needs to be 7.2. If the pH needs to be adjusted upward, do this by adding 0.1N NaOH. If the pH needs to be adjusted downward, do this by adding 0.1N HCl.

3. Biotinylation Steps a. Dialyze the monoclonal antibody solution in the 0.1M pH 8.2 $NaHCO_3$ solution. Use 1,000 mls of 0.1M pH 8.2 $NaHCO_3$ solution for each 1 ml volume of monoclonal antibody. Dialyze the monoclonal antibody until the pH of the monoclonal antibody solution is pH 8.2. Dialyzation overnight at 4° C. on a stir plate with low speed stirring will usually result in the pH being 8.2. Check pH of monoclonal antibody. Change $NaHCO_3$ solution and continue dialyzation, if it is not at pH 8.2.

b. Mix the pH 8.2 monoclonal antibody solution and NHS-biotin DMSO solution in a ratio of 6 volumes of monoclonal antibody solution to one volume of NHS-biotin DMSO solution.

c. Incubate the monoclonal antibody/NHS-biotin DMSO at room temperature (approximately 25° C.) for 3-4 hours.

d. Place the monoclonal antibody in dialysis tubing and dialyze the monoclonal antibody/NHS-biotin DMSO solution for a minimum of 12 hours in the pH 7.2 PBS solution at 4° C. Change the PBS twice during the dialysis. The volumes should be 2 liters of PBS for each ml of monoclonal antibody NHS-biotin DMSO mixture. Dialyzation is preferably done on a stir plate with low speed stirring.

e. Add Thimerasol at 0.2 mg per ml of the final dialyzed biotinylated monoclonal antibody solution.

f. Test the biotinylated monoclonal antibody using standarized positive and negative sera to determine optimal working concentration of the biotinylated antibody.

Reference—Use the procedures as outlined above - for general reading only—Jackson, S. and Kindt, T., Antiallotypic Antibodies in Methods In Enzymology. Academic Press,Inc. New York City, N.Y., Vol. 116:157-173, 1985.

B. Diagnostic cELISA procedure

I. Materials

A. Equipment
   1. Beckman's BIOMEK 1000 Automated Laboratory Workstation
   2. Vacuum
   3. Plate Shaker
   4. Vortex
   5. Beckman Microtiter Plates B. 17% protein LPS Antigen (1.0 mg/ml in 0.1% $NaN_3$):
   a. Wash the pellet of bacteria with 3 vol. of distilled $H_2O$ and recover by centrifugation at $2.5 \times 10^4$ g for 30 min.
   b. Add same volume of distilled $H_2O$ to the washed bacteria and freeze the suspension at $-20°$ C. to $-60°$ C.
   c. Thaw the frozen bacteria by sonication water bath and collect by centrifugation.
   d. Repeat the freeze-thaw cycle again.
   e. Add the same amount of d $H_2O$ to the ultrasonication treated bacteria and subject to hot phenol extraction with phenol: H2O (45:55) at 66° C. for 25 min.
   f. Centrifuge at $1.3 \times 10^4$g for 20 min. at 4° C.
   g. Draw off upper phenol-saturated $H_2O$ and lipid layer with capillary pipette attached to a vacuum line.
   h. Filter the phenol layer through Whatman 42 filter paper under slightly negative pressure.
   i. Add 3 vol. of cold methanol SA (one part of methanol saturated with sodium acetate to 99 parts methanol) to the fraction of phenol phase.
   j. Mix for 5 min. and place at 4° C. for 1 hour.
   k. Centrifuge for 15 min. at 4° C. at low speed. Discard the supernatant.
   l. Dissolve the precipitate and dialyze against distilled $H_2O$ for 2 days with three changes per day.
   m. Centrifuge the dialyzed material at $2.4 \times 10^4$ g for 2 to 4 hours.
   n. Concentrate the supernatant by membrane filtration (Molecular Weight Cut Off $1.0 \times 10^5$).
   o. Store the nonfilterable fraction at 20 mg/ml $H_2O$ (Take 10 ml in duplicate to lyophilize and calculate the concentration) at $-20°$ C. in 0.1% $NaN_3$.
   p. Prepare working solution at 1.0 mg/ml 0.1% $NaN_3$.

Reference: Wu et al., Mol. Cell Biochem. 75, 93-102, 1987, and Mol. Immun. 21, 1123-1129, 1984.

C. Other Reagents
   1. Test sera
   2. Biotinylated monoclonal Ab #39
   3. Horseradish Peroxidase (HRPO) - Avidin D (Vector Lab.)
   4. Peroxidase Substrate ABTS (2.2'-Azinodi-[3-ethyl-benzthiazoline sulfonate]) system (K&P)

D. Solutions
   1. Double distilled (dd) water
   2. 0.1M HCl
   3. PBS Buffer (see biotinylation procedure)
   4. PBS - Tween Buffer (1.0% Tween 80)

II. Procedure

A. Preparation of Antigen Plate
   1. Make 1/1000 (11 µl/11 ml of 0.1M HCl) dilution of the 17% LPS antigen and pipet 100 µl/well (10 ng/well of LPS) into each well.
   2. Place Beckman microtiter plate in appropriate slot on BIOMEK—put diluted Ag solution in appropriate container (1st slot on tray) on BIOMEK.
   3. Once all wells are loaded, shake plate for about 10 min., rotating plate at halfway point.

B. Binding of Primary Antibodies
   1. Post-Antigen incubation—wash the plate 3X with dd-water. MAKE SURE VACUUM IS ON. Tap dry.
   2. Add 100 µl per well of sera/biotinylated Mab mixture manually in replicates of four. (Sera/Mab mixture consists of equal parts of 1/20 test sera and 1/2500 biotinylated Mab #39). They are diluted as follows:
   Sera: 12.5 µl sera/250 µl PBS-Tween
   Mab: 2.6 µl Mab/6.5 ml PBS-Tween Dilute test sera (sera at RT) then add 250 µl of diluted Mab to each tube.*

*For the positive and negative controls, standard positive control sera (from known infected cows) and standard negative control sera (from non-exposed cows) mixed with the appropriately diluted Mab should compete close to 100% and 0% respectively. The background OD on the plate is determined by using buffer in the place of the sera/Mab mixture.

MIX. LOAD PLATE.
   3. Shake plate for 15 min. (rotating plate halfway through)
   4. Wash plate 3X with PBS-Tween
   5. Tap dry the plate dry.

C. Binding of Secondary Reagents
   1. Add 100 µl of Avidin-Horse radish peroxidase diluted 1/1000 in PBS-Tween to each well.
   2. Shake plate for 15 min. (turning plate halfway through incubation).
   3. Wash plate 5X with PBS-Tween and 1X with PBS. Tap plate dry.

D. Addition of Enzyme System
   1. Add 100 µl of substrate system to each well. The substrate is made by mixing 5.5 ml ABTS with 5.5 ml hydrogen peroxide.
   2 Shake plate only 5 min. Then READ.

E. Reading Plate
   Add 100 µl of water and read plate.

EXAMPLE 4

This example is to a comparison of the specificity and sensitivity of a Mab cELISA according to the present invention with five USDA approved serologic tests.

An analysis of data from preliminary studies developed with the cELISA was used to set the level of competition to differentiate between an antibody response to *B. abortus* S19 vaccine and an antibody response to *B. abortus* S2308 challenge. This primary data set was derived using 65 different sera from 20 cows. Control sera from known culture negative animals were used as a control for 0% competition. Sera from known culture positive animals were used to derive the 100% competition value.

To derive the level of competition between test sera and the Mab that would be differential for infection, the data were transformed by the standard Box-Cox transformation procedure. Box, G. E. P., Cox, D. R., "*Analysis of Transformations*", Journal of the Royal Statistical Society B., Vol. 29 (1964) 211. This was done to equalize the variance between the test results of sera from culture negative and culture positive cows. The transformed data showed that 85.45% competition differentiated the sera from the culture negative and culture positive cows 98.87% of the time.

The cELISA test according to the present invention was performed in a blind fashion on 346 different sera from 190 cows. We performed these latter tests to validate the 85% level of competition, derived from the primary cELISA data set, that differentiates between S19 vaccinal responses and S2308 challenge responses.

Four of the five USDA-approved *B. abortus* serology tests (Card, Rivanol, CF, and PCFIA) that were used for comparison of the sensitivity and specificity with our cELISA were performed by the Texas Animal Health Commission's laboratory personnel at Austin, Tex. A standard anti-brucella ELISA and the cELISA according to the present invention were performed in our laboratories. We supplied the Texas Animal Health Commission with the same sera samples that we tested in our cELISA, and they performed the four USDA-approved *B. abortus* serology tests.

Table 1 set forth below represents a summary of the above mentioned comparison. Efficiency is derived by the ability of each test to correctly identify true negative (TN) and true positive (TP) individual cows. A ratio of the sum of true positive and true negative determined by each test with the sum of actual TP+TN (346) yields the efficiency.

TABLE 1

| Total Tests | | n = 346 | Efficiency |
|---|---|---|---|
| cELISA | TP + TN | n = 319 | 92.196532 |
| Card | TP + TN | n = 243 | 70.231214 |
| Rivanol | TP + TN | n = 253 | 73.121387 |
| CF | TP + TN | n = 298 | 86.127168 |
| ELISA | TP + TN | n = 221 | 63.872832 |
| PCFIA | TP + TN | n = 262 | 75.722543 |

From these data it becomes quite evident that the cELISA assay is much more efficient than any other USDA serologic test for field strain infection and does not detect antibody stimulated by strain 19, as early as three weeks post-vaccination. The cELISA has a somewhat reduced sensitivity, but became nearly 100% sensitive at 11 weeks post-challenge in known status animals. Thus, in field applications of this test, it may be desirable to add a third category of suspect animals somewhere in the range of 65% to 85% competition. Some other assays were able to detect a higher percentage of infected cows a few weeks earlier, but it is noteworthy that only one of the tests was 100% sensitive prior to 11 weeks post-challenge. The single exception was the Rivanol test at 3 weeks post-challenge. However, at 8 weeks post-challenge, the sensitivity of the Rivanol test dropped to 71.4%.

Another added advantage to the cELISA is that it can be run on most commercially available manual or automated ELISA equipment which is currently used in most central laboratories. The other major advantage of this assay is that it is based upon a standard reagent, a biotinylated Mab, competing with the bovine antibodies in the test serum for a specific antigenic determinant on the lipopolysaccharide of *B. abortus*, giving it a very high degree of specificity.

The preceding description of specific embodiments of the invention is intended to illustrate the invention, not to provide an exhaustive list of all possible embodiments. Those skilled in the art will recognize that changes can be made to the specific embodiments described above without departing from the spirit and the scope of the present invention.

What is claimed is:

1. A competitive immunoassay for differentiating a sample containing antibodies stimulated by a *B. abortus* field strain infection form a sample containing antibodies estimated by *B. abortus* Strain 19 vaccination comprising the following steps:

a) providing a quantity of a biotin-conjugated monoclonal antibody produced by a hybridoma cell line having ATCC deposit number HB10286;

b) obtaining a test sample from an animal, wherein said test sample is milk or serum;

c) admixing said biotin-conjugated monoclonal antibody with said test sample in a container which contains a quantity of immobilized *B. abortus* lipopolysaccharide antigen;

d) incubating said admixture from Step (c) to allow competition between biotin-conjugated monoclonal antibody and antibodies in said test sample for specific binding to said immobilized lipopolysaccharide antigen;

e) washing said container so as to remove any unbound monoclonal antibody;

f) adding avidin-enzyme conjugate and substrate to measure the quantity of the biotin-conjugated monoclonal antibody bound to said lipopolysaccharide antigen;

g) calculating the percent competitive inhibition wherein greater than about 65% and less than or equal to about 85% inhibition is suspect for *B. abortus* field strain infection and greater than about 85% inhibition is positive for *B. abortus* field strain infection.

2. The competitive immunoassay of claim 1 wherein said *Brucella abortus lipopolysaccharide* antigen is unpurified.

3. The competitive immunoassay of claim 2 wherein said *Brucella abortus lipopolysaccharide* antigen contains about 13% to about 17% protein.

4. A mercantile kit useful in performing immunoassays for differentiating a sample containing antibodies stimulated by *B. abortus* field strain infection from a sample containing antibodies stimulated by *B. abortus* Strain 19 vaccination which comprises multiple containers wherein one of said containers has therein a solution including a monoclonal antibody produced by a hybridoma cell line having ATCC deposit number HB10286.

5. The mercantile kit according to claim 4 wherein said monoclonal antibody is conjugated to biotin or conjugated to an enzyme.

6. A competitive immunoassay for differentiating a sample containing antibodies stimulated by a *B. abortus* field strain infection from a sample containing antibodies stimulated by *B. abortus* Strain 19 vaccination comprising the following steps:
  a) providing a quantity of a enzyme-conjugated monoclonal antibody produced by a hybridoma cell line having ATCC deposit number HB10286;
  b) obtaining a test sample from an animal suspected of having a *B. abortus* infection, wherein said test sample is milk or serum;
  c) admixing said enzyme-conjugated monoclonal antibody with said test sample in a container which contains a quantity of immobilized *B. abortus* lipopolysaccharide antigen;
  d) incubating said admixture from Step (c) to allow competition between enzyme-conjugated monoclonal antibody and antibodies in said test sample for specific binding to said immobilized lipopolysaccharide antigen;
  e) washing said container so as to remove any unbound monoclonal antibody;
  f) adding substrate to measure the quantity of the enzyme-conjugated monoclonal antibody bound to said lipopolysaccharide antigen; and
  g) calculating the percent competitive inhibition wherein greater than about 65% and less than or equal to about 85% inhibition is suspect for *B. abortus* field strain infection and greater than about 85% inhibition is positive for *B. abortus* field strain infection.

7. The competitive immunoassay of claim 17 wherein said *Brucella abortus* lipopolysaccharide antigen is unpurified.

8. The competitive immunoassay of claim 7 wherein said *Brucella abortus* lipopolysaccharide antigen contains about 13% to about 17% protein.

9. A hybridoma on deposit with the American Type Culture Collection having ATCC deposit number HB10286.

10. A monoclonal antibody produced by the hybridoma cell line of claim 9.

* * * * *

UNITED STATES PATENT AND TRADEMARK OFFICE
CERTIFICATE OF CORRECTION

PATENT NO. : 5,190,860
DATED : March 2, 1993
INVENTOR(S) : Leslie G. Adams, et al.

It is certified that error appears in the above-identified patent and that said Letters Patent is hereby corrected as shown below:

Column 3, Line 45, insert -- . -- after "screened".

Column 7, Line 4, change "un&il" to -- until --.

Column 9, Line 40, change "H2O" to -- $H_2O$ --.

Claim 1, Line 18, change "form" to -- from --.

Claim 1, Line 19, delete "estimated" and replace with -- stimulated --.

Claim 1, Line 41, insert -- and -- after "antigen;".

Claim 7, Line 10, delete "17" and replace with -- 6 --.

Signed and Sealed this

Twenty-first Day of December, 1993

*Attest:*

BRUCE LEHMAN

*Attesting Officer*   *Commissioner of Patents and Trademarks*